US006841696B2

(12) United States Patent
Kraus et al.

(10) Patent No.: US 6,841,696 B2
(45) Date of Patent: Jan. 11, 2005

(54) N-UNSUBSTITUTED AMIDINIUM SALTS

(75) Inventors: Helmut Kraus, Odenthal (DE); Rosemarie Wodarsch, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/228,654

(22) Filed: Aug. 27, 2002

(65) Prior Publication Data

US 2003/0060653 A1 Mar. 27, 2003

(30) Foreign Application Priority Data

Aug. 30, 2001 (DE) ......................................... 101 42 335

(51) Int. Cl.$^7$ .......................................... C07C 253/00
(52) U.S. Cl. ..................................... 558/308; 538/318
(58) Field of Search .......................... 558/47, 308, 318

(56) References Cited

U.S. PATENT DOCUMENTS 4,716,243 A     12/1987    Ernst et al. .................. 225/395

FOREIGN PATENT DOCUMENTS

| JP | 60-84254 | 5/1985 |
|---|---|---|
| RO | 59061 | 10/1975 |
| WO | 00/53586 | 9/2000 |

OTHER PUBLICATIONS

Shilcrat et al: "A New Regioselective Synthesis of 1,2, 5–Trisubstituted 1–H–Imidazoles and Its Application to the Development of Eprosartan" Journal of Organic Chemistry, American Chemical Society. Easton, US, Bd. 62, Nov. 28, 1997, Seiten 8449–8454, XP002153509 ISSN: 0022–3263 *Seite 8451; Tabelle 1* *Schema 1*.

Lawrence A. Reiter: "Synthesis of 2–Substituted 5–Acetyl–1–(H)–imidazoles via 3–Chloro–4, 4–Dimethoxy–2–butanone and Related 3,4–Disubstituted 3–Buten–2–ones" J. Org. Chem. Bd. 49, Nr. 19, 1984, Seiten 3494–3498, XP002262682 *Schema 1, Tabelle 1*.

Database Crossfire Beilstein [Online] Beilstein Institut Zur Foerderung Der Chemischen Wissenschaften, Frankfurt AM Main, DE; retrieved from XFIRE Data–base accession No. Reaction ID: 705150 XP002262701 *Zusammenfassung* & IWATSU: Yakugaku Zasshi, Bd. 72, 1952, Seite 366.

Acta Chem. Scand., B 35, (month unavailable) 1981, p. 605, Ingolf Crossland & Frank S. Grevil, "A Convenient Preparation of Acetamidine".

Organic Syntheses, vol.1, (date unavailable), pp. 3–4, Submitted by G.H. Coleman and A.M. Alvabado, Checked by H.T. Clarke and E.R. Taylor, "Acetamide".

Acta Cryst. C40, (month unavailable) 2984, pp. 297–299, R. Norrestam, "Structure of Bis(acetamidinium), Carbonate Monohydrate, $2(C_2H_7N_2+).CO^2{}_3H_2O_1$ at 108K".

Kantlehner, Willi et al: "Study of the effectiveness of various 1–(dialkylamino)–1–methoxycar–benium methyl sulfates for acetalization" Liebigs Annalen Der Chemie, Bd. 2, 1980, Seiten 246–252, XP009009050 *Vebindung 5d* *Seite 247; Tabelle*.

Sandler, S.R. and Karo, W.: "Organic Functional Group Preparations III" 1989, Academic Press, San Diego; CA USA XP002238452 *Seite 250—Seite 255*.

Sandler, S.R. and Karo, W.: "Organic Functional Group Preparations III" 1989, Academic Press, San Diego, CA USA XP002238453 *Seite 338—Seite 339*.

Sandler, S.R. and Karo, W.: "Organic Functional Group Preparations III" 1989, Academic Press, San Diego, CA USA XP002238454 *Seite 314—Seite 321*.

Crossland, I. et al: "A Convenient Preparation of Acetamidine" Acta Chem. Scand., 1981, Seite 605 XP009009009 *das ganze Dokument*.

Norrestam, R.: "Structure of Bis(acetamidinium) Carbonate Monohydrate, 2(C2H7N2+) .C032–H20, at 108 K" Acta Cryst., Bd. C40, 1984, Seiten 297–299, XP009009008 *Zusammenfassung*.

*Primary Examiner*—Rita Desai
*Assistant Examiner*—Robert Shiao
(74) *Attorney, Agent, or Firm*—Diderico van Eyl; Godfried R. Akorli

(57) ABSTRACT

The invention relates to N-unsubstituted imidic ester alkyl sulphates, N-unsubstituted amidinium alkyl sulphates and a process for their preparation, which is characterized in that carboxamides are converted with sulphuric diesters into the corresponding imidic ester alkyl sulphates, which are reacted further with ammonia to give the analogous amidinium alkyl sulphates.

5 Claims, No Drawings

N-UNSUBSTITUTED AMIDINIUM SALTS

BACKGROUND OF THE INVENTION

1. Field of the Invention

The invention relates to N-unsubstituted amidinium salts, to precursors thereof and to a process for their preparation.

2. Brief Description of the Prior Art

N-unsubstituted amidines and their salts, called amidines and amidinium salts for simplicity hereinafter, are valuable synthons in the preparation of heterocyclic compounds. Such compounds have diverse applications in particular in the drugs sector and in crop protection. For example, vitamin B1, eprosartan and conivaptan can advantageously be prepared from alkylamidines or alkylamidinium salts.

Alkylamidinium salts such as, for example, acetamidinium chloride are prepared industrially by the so-called Pinner synthesis (Organic Synthesis Col. Vol. I, S: 4; RO 59061; Izobreteniya 1995(32), 264). This entails initial synthesis of the corresponding imidic ester hydrochloride from acetonitrile, methanol and HCl.

In the literature, the term imidic ester is also frequently referred to as imido ester, imino ester, imido ether, imidate or imino ether, but these are equivalent.

In a second step, the imidic ester hydrochloride, which is sparingly soluble and is therefore isolated as intermediate, is metered with a metering screw into an ammonia solution. This results in the acetamidine hydrochloride, which is likewise sparingly soluble. The described process has the disadvantage that, because of the great hygroscopicity and thermal instability of the intermediate, and its use as solid, special technical precautions are necessary to avoid losses. For the same reasons, handling of the solid acetamidine hydrochloride is not advantageous either.

These disadvantages can, according to JP-A-60-84254, be avoided if acetonitrile and hydrogen chloride are reacted together in a particular ratio. Use of 1.35 to 2 equivalents of hydrogen chloride results in a suspension, while a solution is obtained with more than 2 equivalents. This excess acid must, however, be very carefully neutralized before the reaction with ammonia in order to avoid overheating and the thermal decomposition mentioned previously. This measure means an additional reaction step and the formation of unwanted quantities of salt and is therefore not advantageous for industrial implementation.

There was thus a need to develop an industrially utilizable process for preparing amidines and amidinium salts which very substantially avoids additional neutralization steps or the technically elaborate intermediate isolation of sparingly soluble imidic ester salts.

SUMMARY OF THE INVENTION

A process for preparing amidinium salts has now been found, comprising:

a) reacting carboxamides of the general formula (I)

in which
n is one or two and, depending on n,
for n=1
$R^1$ is $C_1$–$C_{12}$-alkyl, $C_2$–$C_8$-alkenyl, $C_1$–$C_{12}$-haloalkyl or $C_7$–$C_{12}$-arylalkyl or substituents of the general formula (II)

$$A\text{-}B\text{-}D \tag{II}$$

in which, independently of one another,
A is a $C_1$–$C_4$-alkylene radical and
B is a carbonyl group and
D is $R^2$ or $OR^2$,
where $R^2$ is $C_1$–$C_6$-alkyl, or
B and D together are a cyano group, and for n=2
$R^1$ is $C_1$–$C_6$-alkylene or $C_2$–$C_6$-alkenylene, with at least one sulphuric diester of the general formula (III)

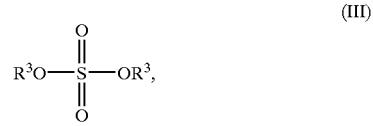

in which the $R^3$ radicals are each, independently of one another, $C_1$–$C_6$-alkyl,
to give imidic ester alkyl sulphates of the general formula (IV)

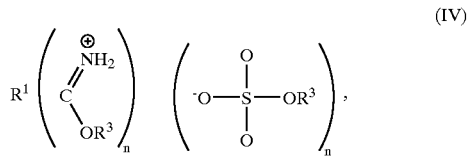

in which
n, $R^1$ and, in each case independently of one another, the $R^3$ radicals have the abovementioned meaning, and b) reacting the imidic ester alkyl sulphates optionally in the presence of a solvent, with ammonia to give the amidinium alkyl sulphates of the general formula (V)

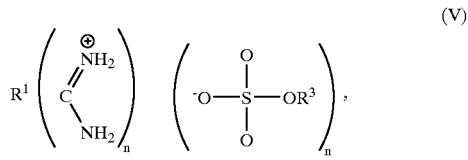

in which
n, $R^1$ and $R^3$ have the above-mentioned meaning.

Alternately, one can obtain amidines of the general formula (VI)

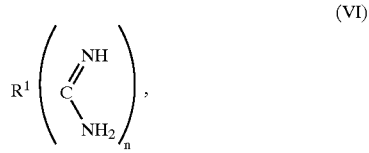

in which
n and $R^1$ have the above-mentioned meanings, from the corresponding amidinium alkyl sulphates of the general formula (V) by addition of base in a manner known per se (see, for example, Acta Chem. Scand., B. 35, 1981, 605).

The amidines of the general formula (VI) can furthermore be converted in a manner known per se into the generally more stable amidine/carbon dioxide adducts (see, for example, Acta Cryst. 1984, C40, 297).

The invention likewise relates both to the imidic ester alkyl sulphates of the general formula (IV) and to the amidinium alkyl sulphates of the general formula (V).

Tautomeric forms of the compounds are likewise included in the scope of the invention. The radicals mentioned are defined below.

DETAILED DESCRIPTION OF THE INVENTION

Alkyl for $R^1$ and $R^2$ is, for example, a straight-chain or branched, cyclic or acyclic alkyl radical which may furthermore be substituted by $C_1$–$C_4$-alkoxy. $C_1$–$C_4$-alkoxy radicals are methoxy, ethoxy, n-propoxy, isopropoxy, n-butoxy, sec-butoxy and tert-butoxy.

The alkyl radicals mentioned may be, for example: for $C_1$–$C_4$ methyl, ethyl, n-propyl, isopropyl, n-butyl, isobutyl or tert-butyl, for $C_1$–$C_6$ additionally n-pentyl, cyclopentyl, n-hexyl and for $C_1$–$C_{12}$ additionally cyclohexyl, n-octyl, isooctyl, n-decyl and n-dodecyl.

Further examples which may be mentioned are methoxymethyl, ethoxymethyl, 2-ethoxyethyl, 2-(2-ethoxyethoxy)ethyl, (2-ethoxyethoxy)methyl and (2-methoxyethoxy)methyl.

Alkyl for $R^3$ is, for example, a straight-chain or branched, cyclic or acyclic alkyl radical such as, for example, methyl, ethyl, n-propyl, isopropyl, n-butyl, isobutyl, n-pentyl, n-hexyl and cyclohexyl.

Alkylene for the purposes of the invention is, for example, a straight-chain or branched, cyclic or acyclic alkylene radical such as, for example, methylene, 1,1-ethylene, 1,2-ethylene, 1,3-propylene, 2,3-propylene, 2,2-propylene, 1,4-butylene, 2,3-butylene, 1,2-cyclopentylene and 1,2-cyclohexylene.

Alkenyl for the purposes of the invention is, for example, a straight-chain or branched alkenyl radical.

Examples thereof are vinyl, allyl, 1-methylvinyl and 2-methylvinyl.

Alkenylene for the purposes of the invention is, for example, a straight-chain or branched alkenylene radical.

Examples thereof are 1,2-ethenylene, 1,1-ethenylene, 1,2-propenylene, 2,3-butenylene, 2-methyl-1,1-ethenylene and 2,2-dimethyl-1,1-ethenylene.

Haloalkyl for the purposes of the invention is, for example, a straight-chain or branched, cyclic or acyclic alkyl radical in which one, more than one or all hydrogen atoms are replaced by halogen atoms which are selected, independently of one another, from the group of chlorine and fluorine.

Examples thereof are fluoromethyl, chloromethyl, dichloromethyl, difluoromethyl, chlorofluoromethyl, dichlorofluoromethyl, chlorodifluoromethyl, trifluoromethyl, trichloromethyl, 2,2,2-trichloroethyl, pentafluoroethyl, heptafluoro-n-propyl and nonafluoro-n-butyl.

Arylalkyl for the purposes of the invention is, for example, a straight-chain or branched alkyl radical which is substituted by at least one aryl radical. The aryl radical(s) may furthermore in turn be substituted. Phenyl is preferred as aryl radical.

Arylalkyl radicals may be, for example: benzyl, 1-methylbenzyl, o-, m-, p-methylbenzyl and o-, m-, p-methoxybenzyl.

Examples of substituents of the general formula (II) are: cyanomethyl, cyanoethyl, methoxycarbonylmethyl, methoxycarbonylethyl, ethoxycarbonyl methyl, ethoxycarbonylethyl and acetyl methyl.

The carboxamides preferably employed for the process according to the invention are those of the general formula (I) where n is 1 and $R^1$ is $C_1$–$C_6$-alkyl, $C_1$–$C_6$-haloalkyl or benzyl.

The carboxamides of the general formula (I) particularly preferably employed for the process according to the invention are those where n is 1 and $R^1$ is methyl, ethyl or 1-methylethyl.

The amide of acetic acid (acetamide) is very particularly preferably employed for the process according to the invention.

Sulphuric diester of the general formula (III) is preferably employed for the process according to the invention.

Preferred sulphuric diesters of the general formula (III) are those in which both $R^3$ radicals are the same and are methyl, ethyl, n-propyl or n-butyl.

The dimethyl ester of sulphuric acid (dimethyl sulphate) is particularly preferred.

Step a) can, if appropriate, be carried out in the presence of solvent.

Suitable solvents for step a) are, for example, aliphatic or aromatic hydrocarbons such as n-hexane, the isomeric hexanes or mixtures thereof, cyclohexane, toluene, o-, m-, p-xylene, halogenated hydrocarbons such as, for example, chloroform, dichloroethane or chlorobenzene, ethers such as tetrahydrofuran, dioxane, dimethoxyethane (glyme), diethoxyethane, diglyme or methyl tert-butyl ether or mixtures of such solvents.

Step a) is preferably carried out without solvent.

The reaction temperature for step a) can be, for example, 20 to 130° C., preferably 50 to 100° C.

The pressure is generally not critical and may be, for example, 0.1 to 20 bar, preferably 0.8 to 1.2 bar.

The molar ratio of carboxamide groups to sulphuric diester of the general formula (III) may be, for example, 0.4 to 3, preferably 0.9 to 1.5, particularly preferably 1.0 to 1.1. It is possible but uneconomic to use larger amounts of sulphuric ester.

Step a) can preferably be carried out in such a way that the carboxamide, where appropriate dissolved in solvent, is added to the sulphuric diester, where appropriate in the solvent.

It is particularly preferred for the carboxamide to be added to the sulphuric diester, each undiluted.

The imidic ester alkyl sulphates of the general formula (IV) obtained in this way can, because of their surprising stability, be either isolated and stored or immediately reacted further. Immediate further reaction is preferred.

Step b) can, where appropriate, be carried out in the presence of solvent. Suitable solvents for step b) are, for example, aliphatic or aromatic hydrocarbons such as n-hexane, the isomeric hexanes or mixtures thereof, cyclohexane, toluene, o-, m-, p-xylene, halogenated hydrocarbons such as, for example, chloroform, dichloroethane or chlorobenzene, ethers such as tetrahydrofuran, dioxane, dimethoxyethane (glyme), diethoxyethane, diglyme or methyl tert-butyl ether, alcohols such as methanol, ethanol, isopropanol, n-butanol, isobutanol or tert-butanol or mixtures of such solvents.

Step b) is preferably carried out without solvent or in the presence of methanol, ethanol or isopropanol or mixtures of these alcohols.

Step b) is particularly preferably carried out in the presence of methanol.

The molar ratio of ammonia to imidic ester alkyl sulphate groups can be, for example, 0.4 to 3, preferably between 0.9 and 1.5, particularly preferably between 1.0 and 1.2. A larger amount of ammonia is possible and can, in liquefied form, itself serve for example as solvent.

The reaction temperature can be, for example, between −40 and 100° C., preferably between 10 and 50° C.

The pressure of the reaction can be, for example, 0.5 to 100 bar, preferably between 0.8 and 2 bar, particularly preferably 0.8 to 1.2 bar. When the process according to the invention is carried out without solvent, the pressure should be chosen so that the ammonia employed is at least partly liquid at the chosen reaction temperature.

For working up, preferably the solvent employed where appropriate, the alcohol liberated during the reaction and, where appropriate, excess ammonia are removed. This can take place, for example, by distillation, for example under reduced pressure.

In a preferred embodiment, the imidic ester alkyl sulphate of the general formula (IV), where appropriate dissolved in solvent, is metered in to an alcoholic ammonia solution.

Liquid imidic ester alkyl sulphates of the general formula (IV) are preferably metered in without solvent.

The amidinium alkyl sulphates of the general formula (V) obtained in this way can be either stored or immediately reacted further.

In a further reaction, free amidines can be obtained from the amidinium alkyl sulphates of the general formula (V) by addition of base in a manner known per se. Examples of suitable bases are alkali metal alcoholates or hydrides. Sodium and potassium methanolate, ethanolate, isopropanolate and tert-butanolate are preferred. Sodium methanolate is particularly preferred.

It is possible where appropriate for the free amidines to be converted in a manner known per se into a carbon dioxide adduct, the preparation preferably taking place by passing carbon dioxide into a solution of the free amidine.

The amidinium alkyl sulphates according to the invention are particularly suitable for processes for preparing nitrogen-containing heterocycles and compounds which contain nitrogen-containing heterocycles. Examples of such nitrogen-containing heterocycles are imidazoles or pyrimidines. Compounds which contain nitrogen-containing heterocycles are, for example, vitamin B1, and substances used in medicaments, such as, for example, conivaptan and eprosartan and the derivatives of these compounds.

The advantage of the process according to the invention is that the amidinium alkyl sulphates can be prepared in extremely high yields starting from the carboxamides which are of low toxicity compared with the corresponding nitriles. In addition, the imidic ester alkyl sulphates and amidinium alkyl sulphates according to the invention surprisingly show high stability and solubility, which considerably facilitates processing thereof, in comparison with the known processes. In addition, at least some of the said compounds are liquid, which likewise considerably simplifies processing. The ease of handling also makes it particularly advantageous to use them in a process for preparing compounds containing nitrogen-containing heterocycles.

EXAMPLES

Example 1 a) 378 g (3 mol) of dimethyl sulphate were introduced into a 1 l one-necked flask and, while blanketing with dry nitrogen, heated to 65° C. Then, over the course of 30 min, 177 g (3 mol) of acetamide were added in portions. After addition of one third of the total quantity, the temperature was maintained at 65° C. by slight cooling. After the addition was complete, the mixture was stirred at 70° C. for 2 h and then allowed to cool.

b) 60 g of ammonia were passed into 300 ml of dry methanol in a second 1 l one-necked flask. The product from a) was then added dropwise over the course of 30 min at room temperature with gentle cooling. The mixture was then stirred at room temperature for 1 h and subsequently the volatile constituents were stripped off at about 50° C. and about 10 mbar. 504.2 g of liquid crude product which, according to H-NMR, comprised 96.4% acetamidinium methyl sulphate were obtained. This corresponds to a yield of 95.3% of theory over the two stages.

$^1$H-NMR of methyl acetimidate methyl sulphate (CDCl$_3$): 2.49 (s, 3H, CH$_3$—C); 3.73 (s, 3H, MeOSO$_3^-$); 4.23 (s, 3H, OMe); 10.35, 11.0 (each s(broad), 2H, NH$_2$)

$^1$H-NMR of acetamidinium methyl sulphate (CDCl$_3$): 2.30 (s, 3H, CH$_3$—C); 3.68 (s, 3H, MeOSO$_3^-$); 8.03, 8.22 (each s(broad), 3H, C=NH(NH$_2$)).

Example 2

73.1 g of propionamide were reacted with 126 g of dimethyl sulphate in essentially the same manner as described in Example 1 but with the aid of a metering screw. The imidic ester was then added dropwise to a solution of 20 g of ammonia in 100 ml of methanol. After stirring for 1 h, the volatile constituents were stripped off at 40–45° C. and 5 mbar. 182.4 g of crude product were obtained and, according to H-NMR, comprised 96.0% propanamidinium methyl sulphate, corresponding to 95.1% of theory.

Example 3

Isobutyramidinium methyl sulphate was obtained in 93.7% of theory from isobutanamide in essentially the same manner as described in Example 2.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing amidinium salts of the general formula (V), comprising (a) reacting carboxamides of the general formula (I)

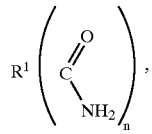 (I)

in which n is 1 or 2 and, depending on n, for n=1

$R^1$ is $C_1$–$C_{12}$-alkyl, $C_2$–$C_8$-alkenyl, $C_1$–$C_{12}$-haloalkyl or $C_7$–$C_{12}$-arylalkyl or substituents of the general formula (II)

-A-B-D (II)

in which, independently of one another,

A is a $C_1$–$C_4$-alkylene radical and

B is a carbonyl group and

D is $R^2$ or $OR^2$, where $R^2$ is $C_1$–$C_6$-alkyl, or

B and D together are a cyano group, and for n=2

$R^1$ is $C_1$–$C_6$-alkylene or $C_2$–$C_6$-alkenylene, with a sulphuric diester of the general formula (III)

$$R^3O-\underset{\underset{O}{\|}}{\overset{\overset{O}{\|}}{S}}-OR^3,$$ (III)

in which the $R^3$ radicals are each, independently of one another, $C_1$–$C_6$-alkyl, to give imidic ester alkyl sulphates of the general formula (IV)

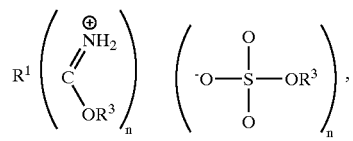 (IV)

in which n, $R^1$ and, in each case independently of one another, the $R^3$ radicals have the above-mentioned meaning, and b) reacting the imidic ester alkyl sulphates of the general formula (IV) with ammonia to give the amidinium alkyl sulphates of the general formula (V).

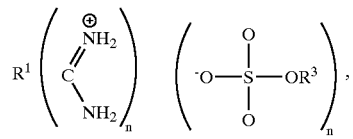 (V)

in which n, $R^1$ and, in each case independently of one another, the $R^3$ radicals have the above-mentioned meaning.

2. The process according to claim 1, wherein step b) is carried out in the presence of solvent.

3. The process according to claim 1 wherein step a) is carried out at 30 to 130° C.

4. The process according to claim 1 wherein step b) is carried out at a temperature of from −40 to 100° C.

5. The process according to claim 1 wherein the sulphuric diester is dimethyl sulphate.

* * * * *